(12) United States Patent
Qvist

(10) Patent No.: US 7,368,128 B2
(45) Date of Patent: May 6, 2008

(54) CONTROLLED RELEASE DRESSING FOR ENZYMATIC DEBRIDEMENT OF NECROTIC AND NON-VIABLE TISSUE IN A WOUND

(75) Inventor: Michael H. Qvist, Koebenhavn Oe (DK)

(73) Assignee: Coloplast A/S, Humlebaek (DK)

( * ) Notice: Subject to any disclaimer, the term of this patent is extended or adjusted under 35 U.S.C. 154(b) by 6 days.

(21) Appl. No.: 10/960,295

(22) Filed: Oct. 8, 2004

(65) Prior Publication Data
US 2005/0113731 A1 May 26, 2005

(30) Foreign Application Priority Data
Oct. 10, 2003 (DK) ............... 2003 01505

(51) Int. Cl.
*A61L 15/00* (2006.01)
(52) U.S. Cl. .................... 424/445
(58) Field of Classification Search ........ 424/445, 424/447; 602/48
See application file for complete search history.

(56) References Cited

U.S. PATENT DOCUMENTS

| | | | | |
|---|---|---|---|---|
| 3,092,552 | A * | 6/1963 | Romans | ............... 424/404 |
| 3,983,209 | A * | 9/1976 | Schmitt | ............... 424/444 |
| 4,122,158 | A | 10/1978 | Schmitt | |
| 4,320,753 | A | 3/1982 | Lenz et al. | |
| 4,668,228 | A | 5/1987 | Bolton et al. | |
| 4,784,653 | A * | 11/1988 | Bolton et al. | ............... 602/54 |
| 5,206,026 | A | 4/1993 | Sharik | |
| 6,043,407 | A | 3/2000 | Lodhi et al. | |
| 6,399,091 | B1 * | 6/2002 | Berthold et al. | ............... 424/443 |
| 2002/0061329 | A1 * | 5/2002 | Leaderman | ............... 424/445 |
| 2002/0114798 | A1 | 8/2002 | Hobson et al. | |

FOREIGN PATENT DOCUMENTS

| | | |
|---|---|---|
| CA | 2 011 220 | 9/1991 |
| EP | 0 296 787 | 12/1988 |
| GB | 2 164 052 | 3/1986 |
| WO | 02/05737 A1 | 1/2002 |

OTHER PUBLICATIONS

The term "derivative", Merriam-Webster Online Dictionary, at the web http://www.m-w.com. p. 1, Jan. 7, 2006.*
Markvicheva E.A. et al., Polymer coatings with immobilized thrombin or peptides: preparation and use for wound healing, Voprosy Meditsinskoi Khimii, 2002, 48(6): 570-576, entire document, with English abstract on p. 576.*
Yudanova T.N. et al., Preparation and properties of medical bandage materials with combined action, Khimicheskaya Tekhnologiya (Moscow, Russian Federation), 2002, 12: 30-33, entire document, (provided with a separate English translation, from STN database search).*
USPTO Translation (in English, pp. 1-9) of Markvicheva E.A. et al. Polymer dressings with encapsulated thrombin or peptides: preparation and use for wound healing, Voprosy Meditsinskoi Khimii, 2002, 48(6): 570-576, entire document, with English abstract.*

* cited by examiner

*Primary Examiner*—Irene Marx
*Assistant Examiner*—Satyendra K. Singh
(74) *Attorney, Agent, or Firm*—Jacobson Holman PLLC

(57) ABSTRACT

A dressing for debridement of necrotic and non-viable tissue in a wound, wherein the dressing comprises an effective amount of one or more proteolytic enzymes incorporated in a degradable polymeric material. The dressing of the invention provides effective debridement of necrotic wounds over a prolonged period of time, as the enzymes may be released over time. As the enzymes are incorporated in the polymeric material, a high stability is achieved.

16 Claims, 5 Drawing Sheets

CONTROLLED RELEASE DRESSING FOR ENZYMATIC DEBRIDEMENT OF NECROTIC AND NON-VIABLE TISSUE IN A WOUND

BACKGROUND OF THE INVENTION

1. Field of the Invention

The invention relates to a dressing such as a wound care dressing being capable of providing enzymatic debridement.

2. Description of the Related Art

In the treatment of chronic wounds it is often a problem that the wound comprises necrotic or non-viable tissue and slough. The presence of these substances renders it difficult for the wound to heal properly as well as it may inhibit the function of the wound dressing by preventing that any active ingredient of the dressing may reach the wound bed. Furthermore, the slough may block/clot the surface of the dressing thus preventing the upper layers of the dressing to function. Finally, the presence of necrotic tissue and slough may give rise to undesired bacterial growth. Therefore it is well known to debride such wounds e.g. by sharp, mechanical or autolytic debridement. It is also possible to use proteolytic enzymes to debride a wound and several ointments and sprays has been marketed for this purpose. Those ointments and sprays typically work within a limited period of time, and thus these products have to be applied repeatedly, e.g. two or three times a day. A consequence of this would be to remove the dressing several times a day for application of ointment, which would be highly undesirable due to the trauma to the skin and the patient as such, during change of dressings. Furthermore, none of these products have the capacity to handle the liquefied slough and degraded necrotic tissue generated by the enzymes.

U.S. Pat. No. 4,668,228 discloses a debriding tape comprising an adhesive mass on a non-gel, non-bioerodable, biocompatible occlusive or semi-occlusive backing, where an effective amount of a debriding enzyme in dry powdered form is situated on the adhesive surface. When the powder is brought into contact with wound exudates the entire load of enzymes is released immediately. This dumping of enzymes may be suitable for burns but it may not be considered optimal when dealing with chronic wounds, where a sustained release of enzyme over a prolonged period often is desired.

CA Patent No. 2,011,220 discloses a material with biological activity comprising a carrier in the form of a textile, an enzyme immobilized on, and covalently bound to the carrier, 0.02-0.50% wt enzyme, 99.50-99.98% wt carrier. When the enzymes are covalently bound to the carrier they may either stay bound during use, or the may be released when a specific enzyme, which is capable of cutting the bond, is present in the wound. If the enzymes stay bound to the carrier, the dressing will only have an effect on the surface of the wound. The enzymes will not reach the deeper layers and the debridement of the wound will be non-sufficient. If an enzyme capable of cutting this bond is present in the wound, the proteolytic enzyme will be released, but the patient-to-patient variation of the amount of enzyme present is typically significant, meaning that the degree of the debridement may vary. Furthermore, in patients suffering from dry necrosis, the enzymes in the wound may not be able to penetrate the necrosis and no therapeutic enzyme will therefore be released. In general, this method will release the greatest amount of debriding enzymes in areas where there is less necrosis and therefore less need of debridement.

In U.S. Pat. No. 5,206,026 is disclosed a film for instantaneously delivery of enzymes to a wound. When exposed to aqueous liquid the film rapidly dissolves, thus releasing its contents of enzymes simultaneously. No long-term release in the form of a controlled release is disclosed; on the contrary, a burst release is desired here.

In US patent application No. 2002/0114798 is disclosed an enzymatic wound debrider that uses a combination of a proteolytic enzyme and an anhydrous hydrophilic poloxamer carrier. The debrider is in the form of an ointment or gel and the reference is silent with respect to any absorbent properties of the debrider as well as the release profile.

Thus there is still a need for a wound dressing being capable of releasing proteolytic enzymes over a prolonged period. This invention has as its primary objective the fulfillment of the above-described need.

SUMMARY OF THE INVENTION

One object of the invention is to provide a wound dressing for easy debridement of chronic wounds.

Another object of the invention is to provide a controlled or sustained release of proteolytic enzymes to the wound.

Yet another object of the invention is to provide an easy and flexible way of incorporation enzymes to a dressing.

Still another object of the invention is to provide an effective debridement of a wound without damaging the surrounding vital tissue.

A further object of the invention is to provide a less painful way of debriding a wound.

A still further object of the invention is to provide an enzyme-containing dressing with a good stability of the proteolytic enzyme during processing and storage of the dressing.

It has surprisingly been shown that these objects are fulfilled by the present invention for debridement of necrotic and non-viable tissue in a wound, wherein the dressing comprises one or more proteolytic enzymes incorporated in a polymeric material that protects the proteolytic enzyme during production and storage of the dressing and furthermore provides a controlled release of the enzymes to the wound.

BRIEF DESCRIPTION OF THE DRAWINGS

The invention is disclosed more in detail with reference to the drawings in which.

DETAILED DESCRIPTION OF THE PRESENT INVENTION

Figure 1:
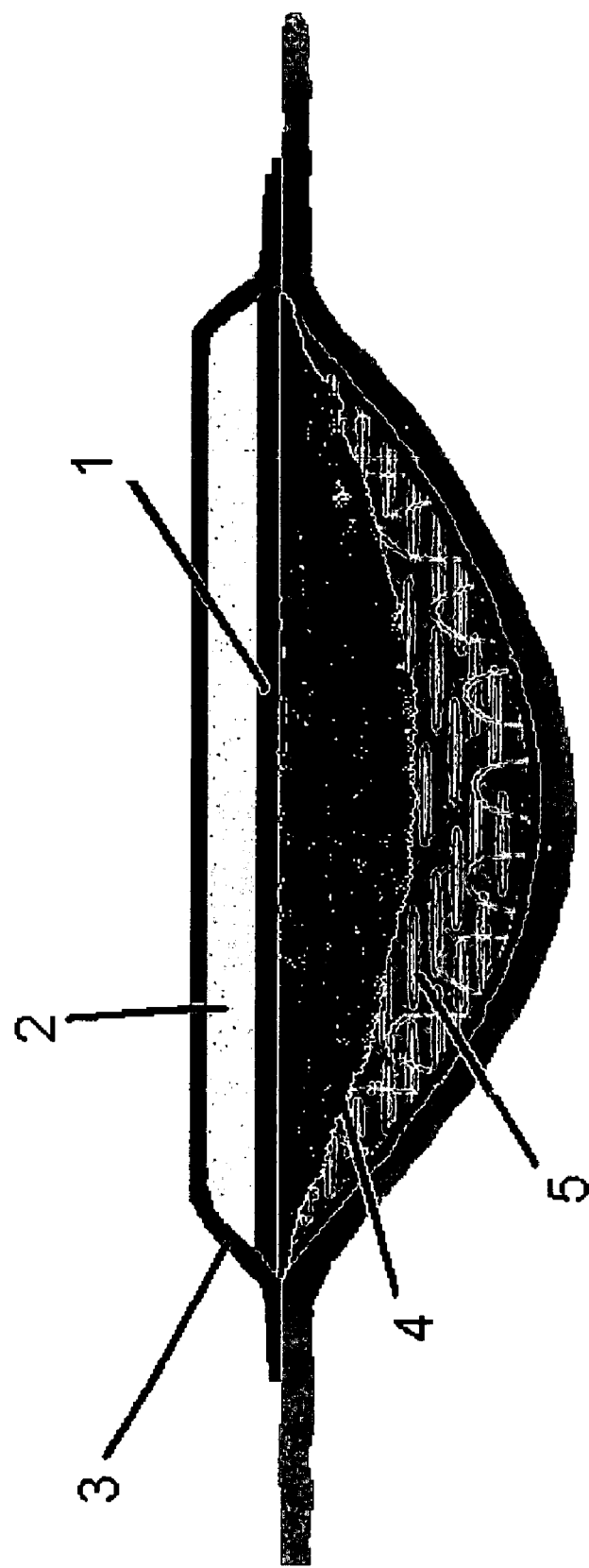
FIG. 1 shows a dressing according to the invention placed on a wound.

The invention relates to a dressing for debridement of necrotic and non-viable tissue in a wound by controlled or sustained release of one or more proteolytic enzymes to the wound, wherein the dressing comprises wound exudates handling means in the form of an absorbent material, and an effective amount of one or more proteolytic enzymes incorporated in a degradable polymeric material, wherein the degradable polymeric material is chosen from the group of celluloses, polyvinyl, polylactates, acrylic polymers, polymers of glycerol and palmitostearic acid, shellac, polyurethanes, gelatine, polyethyleneglycol (PEG) and derivatives and mixtures thereof.

The dressing of the present invention comprises an effective amount of one or more proteolytic enzymes. The enzymes may be in any suitable form and incorporated homogenously or disperse in a polymeric material comprising of one or more polymers. The release of the enzyme may be tailored with respect to various needs. By incorporating the enzyme in a degradable polymeric material a high stability of the enzyme is provided, both during the production of the dressing as well as during storage of the dressing.

Characteristics of Dressing Properties

The dressing of the present invention may be produced in varying sizes depending on the indication, and in an adhesive version as well as a non-adhesive version. Furthermore, the dressings may be in the form of island dressings, with an adhesive flange surrounding an absorbent element, or the dressing may be in the form of a paste or gel, for cavity filling. Preferably, the dressing of the invention is conformable, soft and flexible.

The dressing may comprise a backing layer, e.g. in the form of a film. This layer may preferably be water impervious but vapor permeable. The layer serves as a barrier against bacteria contamination from the surroundings, and at the same time, the vapor permeability renders it possible for the absorbed moisture (exudates) to evaporate, and thus increase the absorbent capacity of the dressing.

The dressing of the invention comprises wound exudates handling means, thereby providing a moist-wound healing environment.

The dressing may be suitable for any wound comprising necrotic tissue including leg ulcers, pressure sores, diabetic foot ulcers and burns. The dressing may be used on low to highly exudating wounds. More preferably, the dressing exhibits good retention properties so that the absorbed wound fluid remains in the dressing even when exposed to (some) compression. In this way the surrounding skin may be protected from maceration.

The wound exudates handling means may comprise absorbent material such as hydrocolloids, foam, e.g. polyurethane foam, alginates, chitosan, super absorbent material, e.g. in the form of particles or fibers, fiber material or it may be in the form of a hydrogel. The absorbent material may preferably be in the form of a layer.

The absorbent layer may have an absorption capacity of 0.9% NaCl aqueous solution at 37° C. of at least 0.05 $g/cm^2$, more preferred at least 0.1 $g/cm^2$, and most preferred at least 0.2 $g/cm^2$, even most preferred at least 0.4 $g/cm^2$. In one embodiment of the invention the absorption is at least 0.6 $g/cm^2$.

In one embodiment of the invention the layer comprises knitted polyester gauze impregnated with petrolatum (65-85%) and carboxymethylcellulose (5-25%). This layer may be used as a wound-contacting layer, which due to the petrolatum, does not stick to the wound.

The dressing may also comprise combinations of the above-mentioned materials in order to obtain optimal wound exudate handling properties.

Characteristics of Enzymes and/or Other Active Ingredients

The dressing is designed to deliver an active component, such as an proteolytic enzyme, to the wound. In dressing constructions where different materials are combined the enzyme may be incorporated in one or more parts of the dressing. The enzyme is incorporated in a polymeric material, and may be integrated in the dressing in different ways.

In one embodiment the polymeric material is in the form of a film on the wound-facing surface of the dressing. A high concentration of the enzyme may be desired on the surface of the dressing contacting the wound bed in order to obtain a more effective debridement due to a high initial release of the enzyme. The film may be in the form of a layer or it may be coated on a net. The film layer may be continuous or discontinuous.

In one embodiment the enzymes and polymeric material are in the form of particles in the dressing. The particles can both be defined with a specific narrow size distribution or have a very wide size distribution pattern. The particles can either be made a) as a homogenous matrix where enzyme and polymer are embedded or b) as a core of enzyme with a coating (shell) of polymeric material or c) as a bi-phase system wherein enzyme and polymer are separated into two phases. Enzyme will, upon wetting, release out trough channels of the polymer. As a special type of bi-phase system there is IPN (inter penetrating network) where both phases are continuous. A combination of the above principles may also be used. A matrix can be coated with a shell of the same or another polymeric material or several small matrixes may be granulated into larger particles. The granulation may involve the same polymers as the matrix. The coating of the particles may have any suitable thickness depending on the desired release time. Thus the release may be controlled by the thickness of the coating or layer of polymer; a thick layer or coating may degrade slower than a thin coat or layer. Spray drying or fluid bed drying or a combination, fluid spray drying may produce the particles of the above principles.

The incorporation of the enzymes in the polymeric material renders them more stable during storage and production of the dressing as they are protected against external factors resulting in degradation, e.g. due to oxidation, degradation, denaturation, deamidation or autolysis.

The enzymes may be distributed in the absorbent material or the may be present on a surface of the absorbent material. If present on the surface, the combined polymeric material and enzyme may be in the form of a layer and may be provided on the skin-facing surface of the absorbent layer for close contact to the wound, or it may be coated on the surface facing away from the wound in order to avoid direct contact to the wound.

Characteristics of Polymeric Material

The properties of the polymeric material may control the release of enzyme in either a controlled or sustained release, or a burst release followed by a controlled or sustained release. The release may be due to several mechanisms, according to the chemical nature of the polymeric material and the physical method of incorporation of enzyme in the polymeric material.

When the dressing is brought into contact with moisture, e.g. in the form of wound exudate, water-molecules causes the polymer to degrade and thereby release the enzymes gradually. The mechanism of degradation of the polymer can be either chemical degradation, dissemble of polymeric chains or swelling. The polymeric material may either absorb water slowly, thereby releasing the enzyme slowly, or the polymeric material may relatively fast absorb water, and then, especially if cross-linked, create a gel on the surface of the particle, which creates a slow release of enzyme.

When the proteolytic enzyme is wetted, the enzymes dissolve, and diffuse from the polymeric material and out of the dressing. The polymers may be intelligent and only release the enzyme at a specific pH optimum or if a specific trigger compound, preferably a compound only present in chronic wounds is present.

Even a small amount of moisture may activate the release from the polymer and thus provide a suitable release from the dressing. The dressing may be available in different variations, according to wound exudate levels. E.g. an easily degradable polymer may provide a adequate release even when only low amounts of moisture is present, and a slowly degradable polymer may be desired when used on highly exuding wound in order to avoid release of all of the enzymes at once.

In one embodiment of the invention the wound exudates is only absorbed vertical in the dressing and thereby only facilitate release of proteolytic enzyme where exudating wound surfaces the dressing and thereby minimizes the amount of enzyme reaching the surrounding intact skin.

A controlled release may be obtained by having a polymeric material comprising at least two polymers, wherein one of the polymers is degraded faster than the other polymer. For example the controlled release may be achieved by coating enzymes in the form of particles with a degradable polymeric material and then incorporating the coated particles in a degradable polymer in the form of a film. The two degradable polymers may be different or the same, preferably the polymeric material selected for the film layer is degraded faster than the polymeric material selected for the coating. When wound exudate is absorbed in the dressing, it causes the film to degrade and the coated particles of enzyme are released from the film and transported via the exudates to the wound bed, where the enzyme is released from the particles.

The polymeric material may be selected from polymers having suitable degradation rate when contacted with water (wound exudates). Examples of such suitable polymers are in the following groups:

Celluloses:
    carboxymethyl cellulose (CMC), hydroxyethyl cellulose (HEC), hydroxypropyl cellulose (HPC), ethyl cellulose (EC), hydroxypropylmethyl cellulose (HPMC), polysaccharides, cellulose acetate phthalate (CAP), microcrystalline cellulose (MCC), cellulose acetate butyrate (CAB), cellulose acetate trimellitate (CAT), hydroxypropyl methylcellulose phthalate (HPMCP)

Polyvinyls:
    polyvinylpyrrolidone (PVP), copolymer of vinylpyrrolidone, polyvinyl acetate phthalate (PVAP), polyvinyl alcohol (PVA) and vinylacetate Acrylic Copolymers:
    copolymers of methacrylic acid, methacrylic alkylester, cross-linked polyacrylic acid, Poylactates
    DL-PLG poly(DL-lactide-co-glycolide), DL-PLA poly(DL-lactide), L-PLA poly(L-lactide), PGA poly(glycolide) or PCL poly(e-caprolactone).

Others:
    polymers of glycerol and palmitostearic acid, Shellac, polyurethanes, gelatine, polyethyleneglycol (PEG)

The polymeric material can be used with a range of different molecular weights, grades, degree of substitution and different degrees of cross-linking, and either native in the raw material or induced during production processes.

The polymeric material may be in the form of a film or it may be in the form of a coating of the enzymes. The polymeric material may be incorporated in a layer, which is in direct contact with the wound.

Characteristics of Enzyme

The enzyme(s) suitable for the invention may be proteolytic enzymes capable of degrading devitalized tissue, eschar and slough. The enzyme(s) may be proteolytic enzymes capable of degrading proteins, such as fibrin, denatured collagen and elastin. The enzymes should be debriding when contacted with necrotic tissue but have minimal impact on vital tissue.

The enzyme may preferably be chosen from the group of bromelain, collagenase, fibrinolysin, deoxyribonuclease, krillase, papain, streptokinase, streptodornase, sutilains, subtilisin, trypsin and vibriolysin. The enzyme may be of natural origin or produced by GMO and may be with a very high purity (e.g. 99.9%) or constitute a mixture of enzymes or other entities natural occurring in the origin of the enzyme raw material.

A Preferred Enzyme is Papain.

In a preferred embodiment the enzyme is a refined papain-preparation from the papaya fruit and may thereby contain other active enzymes than the enzyme papain.

The effective amount of enzyme may differ depending upon the desired application as well as the chosen enzymes. In general the amount of enzyme is determined in order to obtain effective debriding properties of the dressing, e.g. so that most wounds are debrided within 14 days of treatment using this/these dressing(s). Preferably, the dressing of the present invention exhibits enzyme activity and debriding properties that begin a few hours after the dressing has been applied and lasts for up to several days. The dressing of the present invention may release enzymes/exhibit enzyme activity over a period of at least 12 hours, more preferred 24 hours, even more preferred 48 hours and most preferred 96 hours. In one embodiment of the invention the dressing exhibits enzyme activity for more than 7 days, more preferred more than 6 days and even more preferred more than 5 days.

For papain, suitable amounts of enzymes in the dressing of the present invention are up to $1 \times 10^7$ USP units per $cm^2$ preferably $1 \times 10^4$ to $2 \times 10^6$ and more preferably $2 \times 10^4$ to $1 \times 10^6$. For other enzymes lower or higher amounts may be appropriate to be equivalent to the described debriding effect of papain.

The enzyme may be activated by different means e.g. when brought in contact with wound exudate. It is preferred that the enzyme activity lasts during the recommended wear time of the dressing, depending on the amount of exudate.

It is preferred that the enzyme activity stretches over a prolonged period of time, as dressing changes often are traumatic for both the wound and the patient. The release or the enzyme activity may be controlled in such a way that a determined amount of enzyme (activity) is released per time unit, this may be the same amount over time, or it may e.g. be a boost shortly after the dressing is applied, followed by a lower release over the next days.

Other Active Agents

Other suitable active agents may be incorporated into the dressing of the invention, such as charcoal to remove odor or hormones that stimulates healing. Other suitable enzymes for debriding, surfactants, such as urea for softening necrotic tissue and expose dead proteinaceous material and stabilizers of the proteolytic enzyme such as cysteine and EDTA may also be present.

In order to control bacteria in the wound bed and to avoid bacteria growth in the dressing during wear time, the dressing may further comprise an antiseptic or antibacterial agent such as a silver compound, hypochlorite, chlorhexidine or other antibacterial compounds known in the art.

The debridement process as well as dressing changes may give rise to pain for the patient, and thus it may be preferred to incorporate a a pain-relieving agent such as an analgesic or an anesthetic compound in the dressing of the present invention.

The dressing of the present invention may further comprise debriding compositions other than enzymes, which may have additive or synergistic debriding effect. An example of such compound may be urea.

The dressing of the invention may also be suitable for use for treatment of skin diseases, such as psoriasis or other forms of skin treatment.

Description of the Preferred Embodiments

FIG. 1 shows a dressing according to the invention placed on a wound in need of debridement. The dressing comprises a degradable film (or impregnated mesh net) with enzymes incorporated therein (1), an absorbent material (2) and a backing film (3). The dressing is placed upon necrotic tissue (4), which in this case covers the entire wound bed (5).

Figure 2:
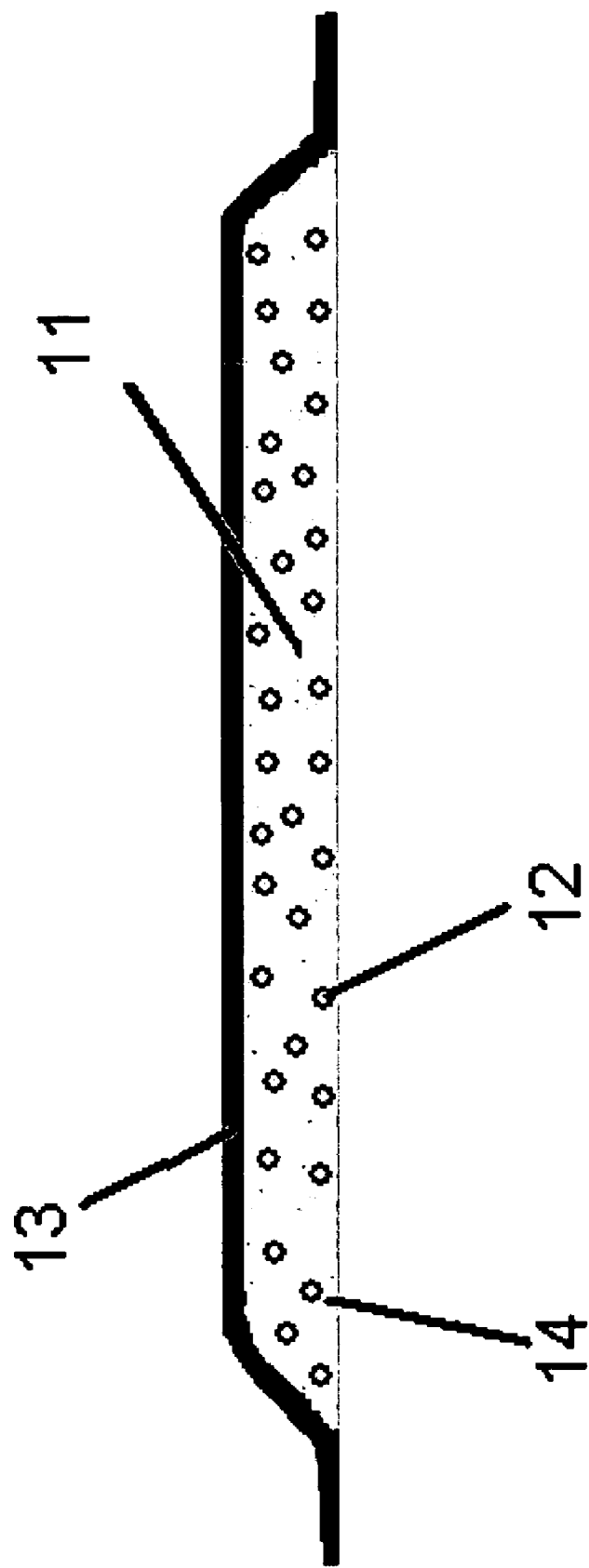
FIG. 2 shows another dressing according to the invention.

FIG. 2 shows another dressing according to the invention comprising enzymes in the form of particles (12) coated with a degradable polymer (14) incorporated in an absorbent material (11). The dressing further comprises a backing film (13).

Figure 3:
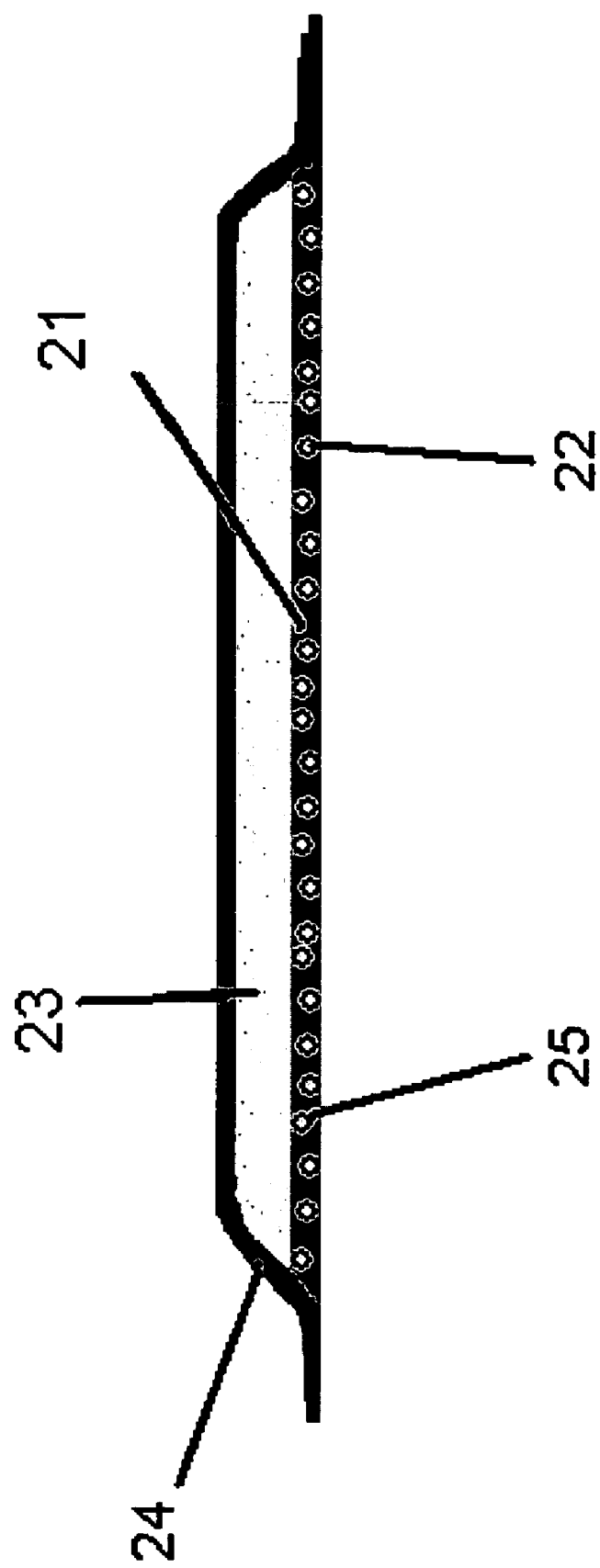
FIG. 3 shows yet another dressing according to the invention.

FIG. 3 shows a dressing according to the invention comprising enzymes in the form of particles (22) coated with a degradable polymer (25) incorporated in a layer of a degradable polymer film (21). The layer may serve as a wound-contacting layer. The dressing further comprises an absorbent material (23) and a backing film (24).

Figure 4:
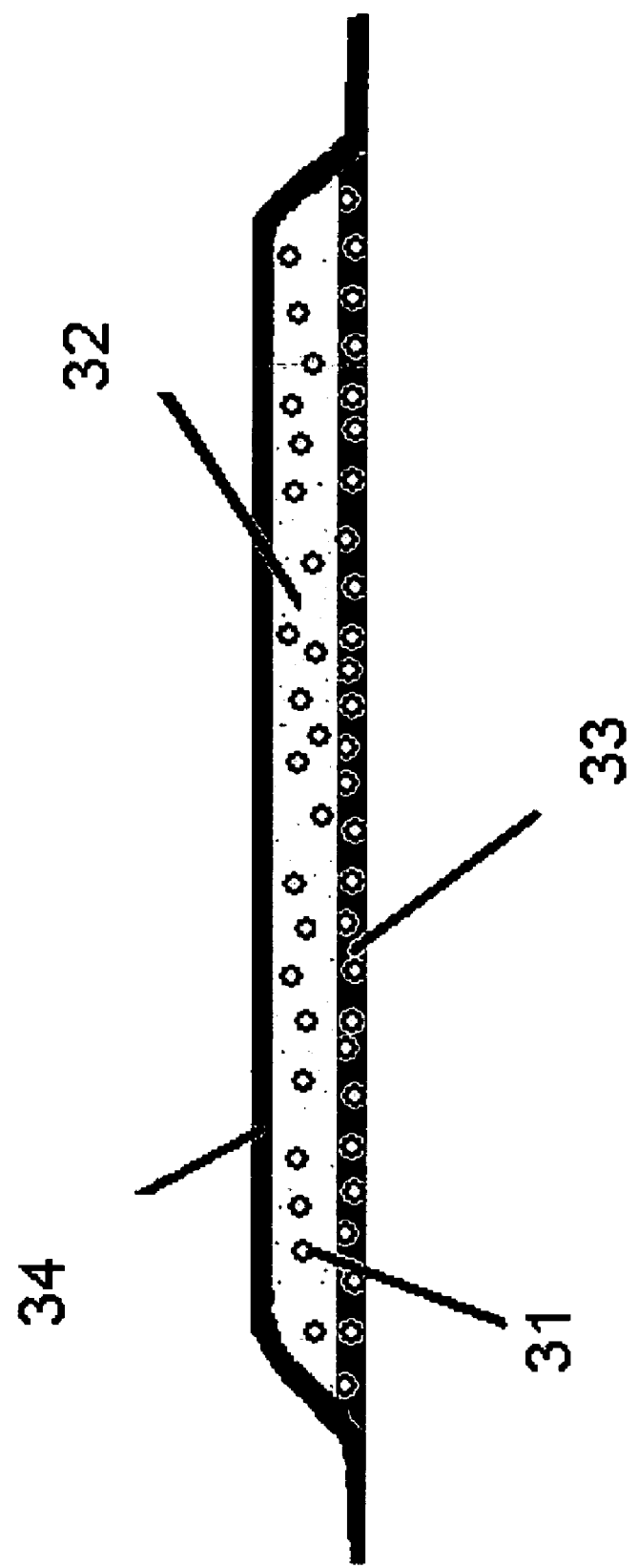
FIG. 4 shows a combination of the embodiments of FIGS. 2 and 3.

FIG. 4 shows a combination of FIGS. 2 and 3, wherein the enzymes in the form of polymer-coated particles (31) are incorporated in both the absorbent layer (32) and the degradable wound contacting film layer (33). The dressing further comprises a backing layer (34).

Figure 5:
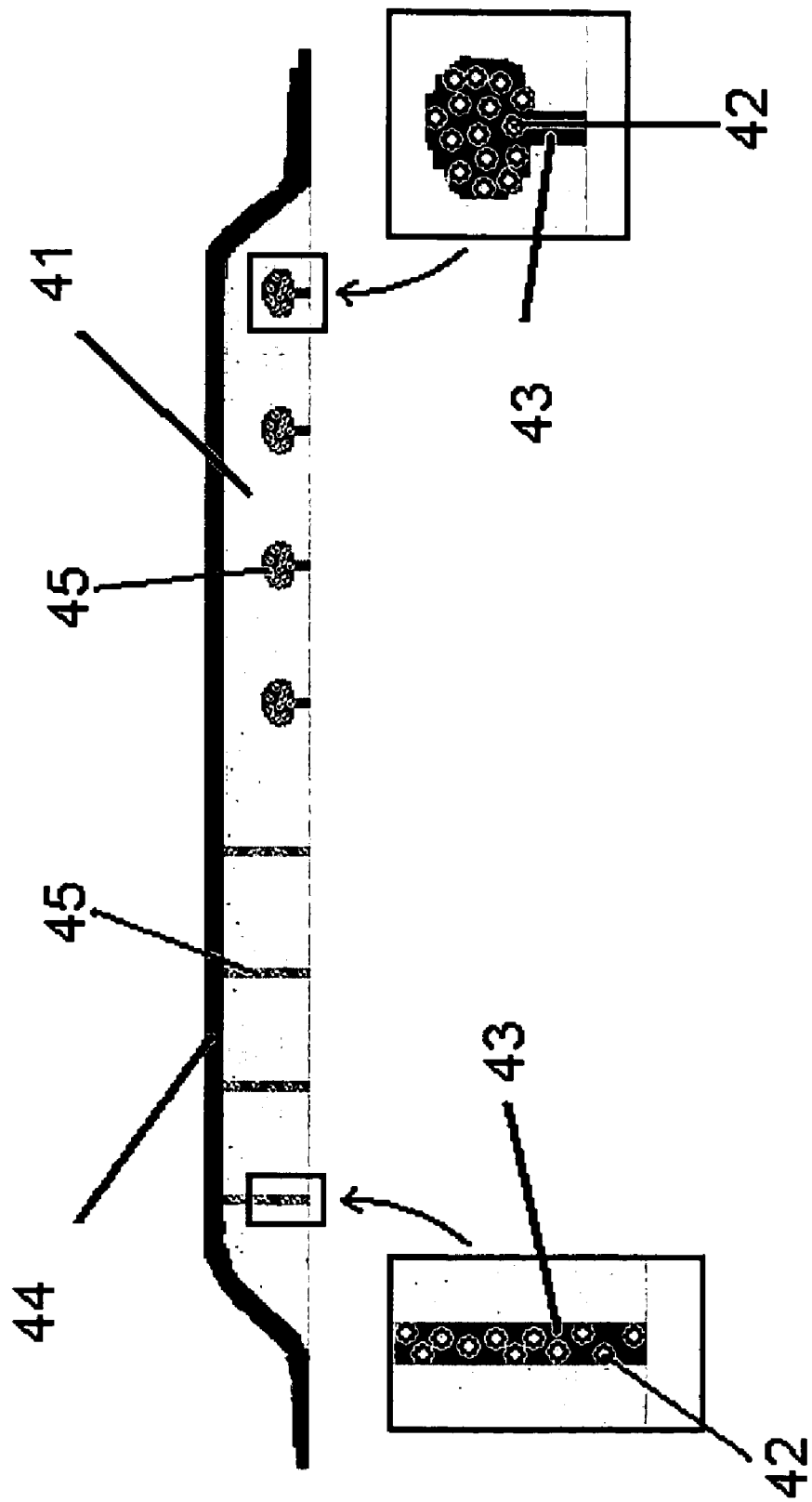
FIG. 5 shows a further dressing according to the invention.

FIG. 5 shows a dressing according to the invention comprising an absorbent material (41), a backing film (44) and a degradable polymeric material (43) placed in vertical canals or cavities (45). The enzymes are in the form of particles (42) incorporated in the degradable polymer material (43).

EXAMPLES

Example 1

Degradable Film on Dressing

A dressing of the kind shown in FIG. 1 was prepared by mixing 8 g Hypol2060 (Dow Chemical Company), 12 g of Hypol 2002 and 20 g of water with 1% w/w Pluronic 62 (BASF AG). The materials were mixed together for approximately 15 seconds. The liquid was poured into a mould and allowed to react for 10 minutes. The resulting foam sheet was dried in an oven at 70° C. for 30 minutes and had a thickness of 3 mm. A polyurethane (PU) backing film was laminated on the top of the foam, thus sealing the dressing from outside. The water permeability of the backing film was 500 g pr m$^2$ pr hour. The foam was supporting the backing film physically and comprised the exudates absorbing properties of the dressing.

A polymer film was casted on a silicone release liner 1022 (Scotch Pak, 3M Medica) using a polymer solution of PVP K90 (5% w/w), K25 (24%), Permulen (5% w/w), Polyurethane, DC-01-1628 (24% w/w), PEG 300 (37% w/w) and papain (5% w/w). When the polymer film was almost dry, it was applied to the foam using a light pressure. A refined release-assay was used, using saline phosphate buffer, pH=7.4. as release medium, wherein the dressing was wetted in approximately the same rate as when a dressing is applied on an average wound and absorbs wound exudate. It was observed that substantially all of the incorporated enzyme was released within 3 hours.

Example 2A

Enzyme Coated in HPC and Embedded in a Polyurethane Foam

A dressing of the kind shown in FIG. 2 was prepared using 500 g of an aqueous solution containing papain (2% w/w) mixed with 10 g of hydroxypropylcellulose (HPC) and spray dried on a Niro FSD 6.5 spray drier, resulting in particles comprising of a homogenous blend of polymer and enzyme in a ratio of 1:1. The mean particles size was 100 µm. A polyurethane foam was prepared as described in Example 1, however the particles were added during mixing of the foam components. In the refined release-assay substantially all the enzyme was released with no significant loss of activity compared to control. 95% of the enzyme was released within 24 hours in a constant release pattern.

Example 2B

Enzyme Coated in HPC and Embedded in a Polyurethane Foam

As in 2A, but instead 20 gr. of HPC was used, thus obtaining a ratio of 2:1 between the polymer and the enzyme. Approximately 95% of the enzyme was released within 36 hours in a constant release pattern.

Example 2C

Enzyme Coated in HPC/Eudragit and Embedded in a Polyurethane Foam

As in 2A but instead of HPC a mixture of HPC and Eudragit 30RL was used in the ratio of 1:1. Approximately 95% of enzyme was released within 48 hours with constant release pattern.

Example 2D

Enzyme Coated in HPMC and Embedded in a Polyurethane Foam

As in 2A but HPC was replaced with hydroxypropylmethylcellulose (HPMC). Approximately 95% of enzyme was released within 72 hours with constant release pattern.

Example 2E

Enzyme Coated in NaCMC and Embedded in a Polyurethane Foam

As in 2B but HPC was replaced with natriumcarboxymethylcellulose (NaCMC). Approximately 95% of enzyme was released within 96 hours with constant release pattern.

Example 2F

Enzyme Coated in PVP and Embedded in a Polyurethane Foam

A 10% w/w solution of enzyme was spray dried. In a fluid bed the particles was coated with PVP. Approximately 95% of enzyme was released within 24 hours with constant release pattern.

Example 2G

Enzyme Directly Embedded in a Polyurethane Foam

As a comparative study, the enzyme was directly embedded in a foam by adding 10 g of an aqueous solution containing papain (10% w/w) with 8 g Hypol2060 (Dow Chemical Company), 12 g of Hypol2002 and 10 g of water with 2 part w/w Pluronic 62 (BASF). A foam sheet was prepared as in Example 1. In the release-assay approximately 10% of the incorporated enzyme were released within 6 hours, while the rest of enzyme is retained in the dressing. A considerable loss of activity was observed.

Example 3A

Enzyme Coated in Particles and Added to a Film

A dressing of the kind shown in FIG. 3 was prepared. 100 g of an aqueous solution containing the enzyme Papain (10% w/w), cysteine (0.1% w/w) and EDTA (0.1% w/w) was added to 10 g of a DL-PGL-polymer (50:50) polymer mixture and spray dried into micro/particles with a particle size in the range of 50-200 μm. 20 g of the coated particles and 10 g of urea were then quickly extruded into a gel of hydroxypropylcellulose (HPC, 30% w/w). With the particles in suspension, the film was directly casted into a film on a silicone release liner and dried for 5 min at 45° C. under airflow. The coat weight of the resulting film was 150 gsm. The film was attached to a 3 mm thick polyurethane foam sheet, prepared as described in Example 1.

Example 3B

Gauze Impregnated with Particles

An enzyme blend containing 10 g Papain, 100 mg cysteine and 100 mg EDTA was mixed into a 100 g polymer solution consisting of ethanol (40% w/w), water (40% w/w) and DL-PGL-polymers (20% w/w). Another mixture comprising 10 g of urea mixed into an equivalent amount of the polymer solution was prepared. The two mixtures were then shortly blended and cotton gauze was impregnated with the polymer solution resulting in a coat weight of 100 gsm. The gauze was placed as a wound contact layer in a dressing with a 3 mm water absorbing layer containing super absorbent fibers as the dressing of EP Patent Application No. 1,303, 239. In the release-assay wound exudate was absorbed by the dressing through the impregnated gauze and upon wetting of the gauze the impregnation was slowly dissolved and enzyme was gradually released. After a short lag time the release followed a zero-order profile with release of 0.3 mg pr. cm$^2$ pr. hour in 72 hours. After 72 hours the amount of enzyme depleted.

Example 3C

Dressing with Combines Burst Release and Controlled Release

A burst release film was prepared by mixing papain (14% w/w), PVP K90, Mw 1,300,000 (9% w/w), PVP K25, Mw 34,000 (12% w/w), PEG400 (21% w/w) and PEG4000 (44% w/w). The mix was melted at 65° C. in a double-screw extruder and with a nozzle coated in a homogenous layer onto a foam sheet prepared as in Example 2A. The thickness of the layer was measured to 88 μm and the papain content to 0.51 mg/cm$^2$. In the release assay it was shown that substantially all of the enzyme of the burst release layer was released within 30 min, while 95% of the enzyme of the foam layer was released within 24 hours in a constant release pattern.

Example 4

Enzyme in a Film Attached to a Polyurethane Foam Sheet, with Enzyme (in Particles)

A dressing of the kind shown in FIG. 4 was prepared. A film was prepared as in Example 1, however instead of attaching the film to a non-active foam, the foam in Example 2B was used. In the release model it was shown that 30% of the total enzyme amount was released within 3 hours, where after the release rate continued with a lower rate. All enzyme was released at 30 hours.

Example 5

Example 5—Foam with Vertical Canals Releasing Enzyme

A polyurethane foam was prepared as in Example 1. Holes of 1 mm in diameter were punched out in the foam in a grid, with 1 hole pr. cm$^2$. A 10% papain solution was spray dried and the powder was mixed with PEG 600 (ratio 50:50) and filled into a syringe. A needle was attached and the holes were filled up and the dressing was allowed to dry. In the release model a zero-order profile was observed with depletion at 72 hours.

Example 6

Enzyme at Top Film

A powder of enzyme was produced as in Example 2A and was poured directly on the backing film. A solution for a polyurethane foam was prepared as in Example 1 and was casted directly on the backing film. The resulting foam sheet was dried in an oven at 70° C. for 30 minutes and had a thickness of 3 mm. The foam was supporting the backing film physically and comprised the exudates absorbing properties of the dressing. In a release assay substantially all the enzyme was released with no significant loss of activity compared to control. After a lag time of 2 hours 95% was released within 48 hours in a constant release pattern.

The invention claimed is:

1. A dressing for debridement of necrotic and non-viable tissue in a wound by controlled or sustained release of one or more proteolytic enzymes to the wound, said dressing comprising,
   1) an absorbent material layer;
   2) an amount of particles effective for debridement of necrotic and non-viable tissue, said particles containing one or more proteolytic, debridement enzymes, said enzyme particles coated with a first degradable polymeric material, the first degradable polymeric material being selected from the group consisting of celluloses, polyvinyl, acrylic polymers, polylactates, polymers of glycerol and palmitostearic acid, shellac, polyurethanes, gelatin, polyethylene glycol (PEG) and derivatives and mixtures thereof;
   3) a layer of a second degradable polymeric material; wherein the second degradable polymer is more quickly degraded than the first degradable polymer; wherein a first side of the absorbent material layer is in contact with the enzyme particles coated with the first degradable polymer; wherein the layer of the second degradable polymer is a film which covers the absorbent material and the enzyme particles; and wherein said dressing has a backing layer covering a second side of the absorbent material layer.

2. The dressing according to claim 1, wherein the enzyme particles are distributed in the absorbent material.

3. The dressing according to claim 1, wherein the enzyme particles are present on a surface of the absorbent material.

4. The dressing according to claim 1, wherein the first polymeric material coating the enzyme particles is in direct contact with the wound.

5. The dressing according to claim 1, wherein the enzyme is papain.

6. The dressing according to claim 1, wherein the dressing further comprises a pain-relieving agent.

7. The dressing according to claim 1, wherein the dressing further comprises an antibacterial agent.

8. The dressing according to claim 1, wherein the dressing further comprises urea.

9. The dressing according to claim 2, wherein the absorbent material comprises polyurethane foam.

10. The dressing according to claim 1, wherein said enzyme particles being incorporated into the layer of degradable polymeric film on a wound facing surface of the dressing.

11. The dressing of claim 10, wherein the degradable polymeric film incorporating the enzyme particles degrades faster than the degradable polymer coating on the particles.

12. The dressing of claim 10, wherein the degradable polymeric film incorporating the enzyme particles is comprised of a polymer solution of polyvinylpyrrolidone, 1-Vinyl-2-pyrrolidinone homopolymer (5% W/W), 1-Ethenyl-2-pyrrolidinone homopolymer (24% W/W), acrylate/C10-30 alkyl acrylate crosspolymer (5% W/W), Polyurethane (24% W/W) and PEG 300 (37% W/W).

13. The dressing according to claim 1, wherein said enzyme particles being incorporated into said absorbent material of the dressing.

14. The dressing of claim 13, wherein said absorbent material comprises polyurethane foam.

15. The dressing of claim 14, also having enzyme particles incorporated into the layer of degradable polymeric film on the wound facing surface of the dressing.

16. The dressing according to claim 1, wherein said enzyme particles are incorporated within vertical canals or cavities extending from openings on a wound facing side of said absorbent material.

* * * * *